US010877456B2

(12) United States Patent
Kumazawa et al.

(10) Patent No.: US 10,877,456 B2
(45) Date of Patent: Dec. 29, 2020

(54) NUMERICAL CONTROL APPARATUS AND MACHINING METHOD

(71) Applicant: Mitsubishi Electric Corporation, Tokyo (JP)

(72) Inventors: Tsuyoshi Kumazawa, Tokyo (JP); Kazuya Nakajima, Aichi (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/349,297

(22) PCT Filed: Mar. 5, 2018

(86) PCT No.: PCT/JP2018/008430
§ 371 (c)(1),
(2) Date: May 13, 2019

(87) PCT Pub. No.: WO2019/171444
PCT Pub. Date: Sep. 12, 2019

(65) Prior Publication Data
US 2020/0264579 A1 Aug. 20, 2020

(51) Int. Cl.
*G05B 11/32* (2006.01)
*G05B 19/18* (2006.01)
(Continued)

(52) U.S. Cl.
CPC ......... *G05B 19/186* (2013.01); *G05B 19/232* (2013.01); *G05B 19/414* (2013.01); *A61B 17/1682* (2013.01); *G05B 19/4141* (2013.01)

(58) Field of Classification Search
CPC ............ A61B 17/1682; G05B 19/4141; G05B 19/414; G05B 19/232; G05B 19/186
(Continued)

(56) References Cited

U.S. PATENT DOCUMENTS

| 4,278,374 | A |   | 7/1981 | Wolosianski |
| 5,307,549 | A | * | 5/1994 | Tsutsumi ............ G05B 19/186 29/27 C |

(Continued)

FOREIGN PATENT DOCUMENTS

| JP | 57-100403 A | 6/1982 |
| JP | 63-99114 A | 4/1988 |

(Continued)

OTHER PUBLICATIONS

International Search Report dated Jun. 5, 2018 for PCT/JP2018/008430 filed on Mar. 5, 2018, 2 pages of International Search Report in Japanese Language only.

(Continued)

*Primary Examiner* — Eduardo Colon Santana
*Assistant Examiner* — Zemenay T Truneh
(74) *Attorney, Agent, or Firm* — Xsensus LLP (57) ABSTRACT

A numerical control apparatus includes: a thread-whirling motor controller controlling, based on a thread lead representing a movement amount of a thread whirling tool per rotation of a workpiece, a reference differential speed representing a difference between a predetermined reference rotational speed of the thread whirling tool and a rotational speed of the workpiece, the number of tool blades of the thread whirling tool, and a workpiece spindle speed representing the rotational speed of the workpiece, a first motor moving the thread whirling tool, a second motor rotating the thread whirling tool, and a third motor rotating the workpiece. The thread-whirling motor controller controls: the first motor based on the thread lead and the reference differential speed; the second motor based on the thread lead, the reference differential speed, the number of tool blades, and the workpiece spindle speed; and the third motor based on the workpiece spindle speed.

16 Claims, 5 Drawing Sheets

(51) Int. Cl.
  *G05B 19/23* (2006.01)
  *G05B 19/414* (2006.01)
  *A61B 17/16* (2006.01)

(58) Field of Classification Search
  USPC .............................. 318/625, 571; 411/263
  See application file for complete search history.

(56) References Cited

U.S. PATENT DOCUMENTS

| | | | |
|---|---|---|---|
| 6,030,162 A * | 2/2000 | Huebner | A61B 17/1682 411/263 |
| 2004/0081519 A1* | 4/2004 | Gainer | B23G 5/18 407/49 |
| 2007/0007926 A1* | 1/2007 | Iwashita | G05B 19/4141 318/625 |
| 2012/0264528 A1 | 10/2012 | Isobe et al. | |
| 2014/0318330 A1 | 10/2014 | Rigolone et al. | |

FOREIGN PATENT DOCUMENTS

| | | |
|---|---|---|
| JP | 05-020801 U | 3/1993 |
| JP | 10-118842 | 5/1998 |
| JP | 11-105015 A | 4/1999 |
| JP | 2008-296331 A | 12/2008 |
| JP | 2015-043126 A | 3/2015 |
| WO | 2011/078365 A1 | 6/2011 |

OTHER PUBLICATIONS

Decision to Grant a Patent received for Japanese Patent Application No. 2018-546716, dated Nov. 20, 2018, 5 pages including English Translation.

* cited by examiner

NUMERICAL CONTROL APPARATUS AND MACHINING METHOD

CROSS-REFERENCE TO RELATED APPLICATIONS

The present application is based on PCT filing PCT/JP2018/008430 filed Mar. 5, 2018, which is incorporated herein by reference.

FIELD

The present invention relates to a numerical control apparatus and a machining method for performing thread cutting.

BACKGROUND

In general thread cutting, it is difficult to cut a thread groove to the desired thread groove depth with a single cutting, and thus a screw having a desired shape is formed by repeatedly cutting a workpiece, which is an object to be machined, a plurality of times.

A machining method referred to as thread whirling is known that can cut a thread groove to the desired thread groove depth with a single machining. In thread whirling, machining is performed by bringing a thread whirling tool having a plurality of blades into contact with a rotating workpiece while the thread whirling tool rotates at a speed different from the rotational speed of the workpiece. Such a machining method is disclosed in Patent Literature 1, for example.

CITATION LIST

Patent Literature

Patent Literature 1: Japanese Patent Application Laid-open No. 2015-43126

SUMMARY

Technical Problem

With the use of thread whirling, it is possible to shorten the process for forming a thread groove. Meanwhile, machining for forming a screw includes, in addition to the process for forming a groove, a process for machining the external shape of a screw into a desired shape. The process for forming the external shape of the screw is performed by turning. By simultaneously performing thread whirling and turning, the external shape is formed while a groove is formed, and it is thus possible to shorten the machining time and improve the efficiency.

Here, in thread whirling, a thread whirling tool is moved in the thread lead direction at a speed synchronized with the rotational speed of a workpiece while the difference between the rotational speed of the workpiece and the rotational speed of the thread whirling tool is kept constant. Synchronization in this description means that the movement speed of the thread whirling tool is determined by the rotational speed of the workpiece, and the movement speed of the thread whirling tool changes as the rotational speed of the workpiece changes. In turning, it is necessary to rotate a workpiece at a rotational speed determined by conditions, such as the size, shape, and material of the workpiece, specifications of a tool used for machining, and the like.

Thus, if the rotational speed of the workpiece is increased up to the speed at which turning can be performed during thread whirling, the rotational speed and movement speed of the thread whirling tool are also increased. However, when the movement speed of the thread whirling tool is increased, a thread groove cannot be accurately machined. Conversely, if the movement speed of the thread whirling tool is reduced in order to accurately machine a thread groove, the rotational speed of the workpiece also decreases and may become lower than the rotational speed at which turning can be performed. That is, with the conventional technologies, it has been difficult to perform turning during thread whirling and machining for forming a screw cannot be performed efficiently.

The present invention has been made in view of the above and it is an object of the present invention to obtain a numerical control apparatus capable of improving the efficiency of machining for forming a screw.

Solution to Problem

In order to solve the above problem and to achieve the object, a numerical control apparatus according to an aspect of the present invention includes: a thread-whirling motor controller to control, on a basis of a thread lead representing a movement amount of a thread whirling tool per rotation of a workpiece, a reference differential speed representing a difference between a predetermined reference rotational speed of the thread whirling tool and a rotational speed of the workpiece, the number of tool blades representing the number of blades of the thread whirling tool, and a workpiece spindle speed representing the rotational speed of the workpiece, a motor that moves the thread whirling tool, a motor that rotates the thread whirling tool, and a motor that rotates the workpiece. The thread-whirling motor controller controls: the motor that rotates the thread whirling tool on a basis of the thread lead and the reference differential speed; the motor that rotates the thread whirling tool on a basis of the thread lead, the reference differential speed, the number of tool blades, and the workpiece spindle speed; and the motor that rotates the workpiece on a basis of the workpiece spindle speed.

Advantageous Effects of Invention

A numerical control apparatus according to the present invention has an effect where machining for forming a screw can be performed efficiently.

DESCRIPTION OF EMBODIMENT

Hereinafter, a numerical control apparatus and a machining method according to embodiments of the present invention are described in detail with reference to the drawings. Note that, the invention is not limited by the embodiments.

Embodiment

First, a machining method performed by using a numerical control apparatus according to the present embodiment is described.

Figure 1:
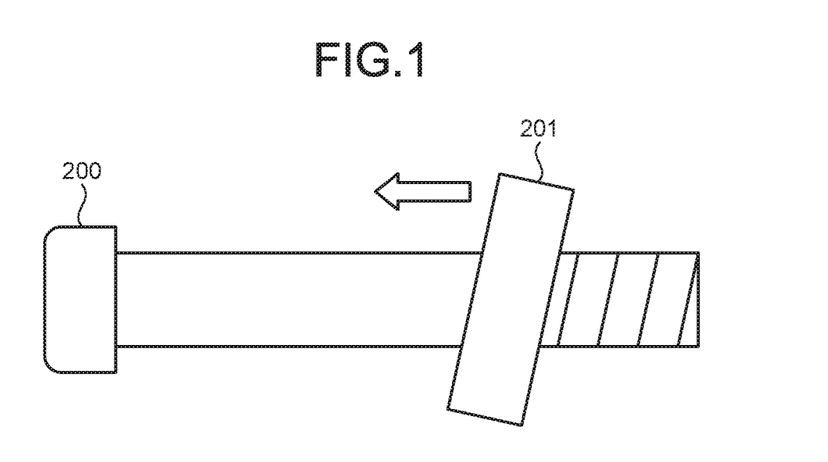
FIG. 1 is a diagram illustrating an operation outline of machining a workpiece to form a thread groove by thread whirling.
Figure 2:
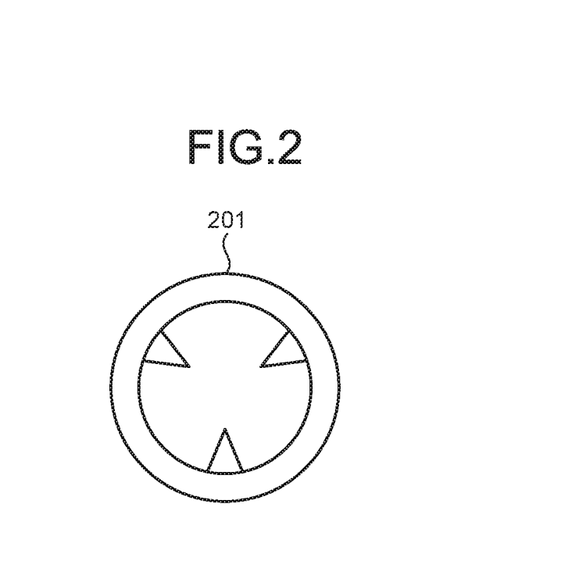
FIG. 2 is a diagram illustrating an example of a thread whirling tool.

FIG. 1 is a diagram illustrating an operation outline of machining a workpiece to form a thread groove by thread whirling. As illustrated in FIG. 1, to form a thread groove by thread whirling, a thread whirling tool 201 is moved in the direction indicated by the arrow while being rotated and inclined with respect to a rotating workpiece 200. The workpiece 200 is thereby cut by the blades of the thread whirling tool 201 brought into contact with the workpiece 200, and a groove is formed. The thread whirling tool 201 has the configuration illustrated in FIG. 2, for example. FIG. 2 is a diagram illustrating an example of a thread whirling tool. The thread whirling tool 201 illustrated in FIG. 2 has three blades on the inner diameter side of an annular tool body. The three blades are equally spaced. In the case where a thread whirling tool has a plurality of blades, the blades are equally spaced.

Figure 3:
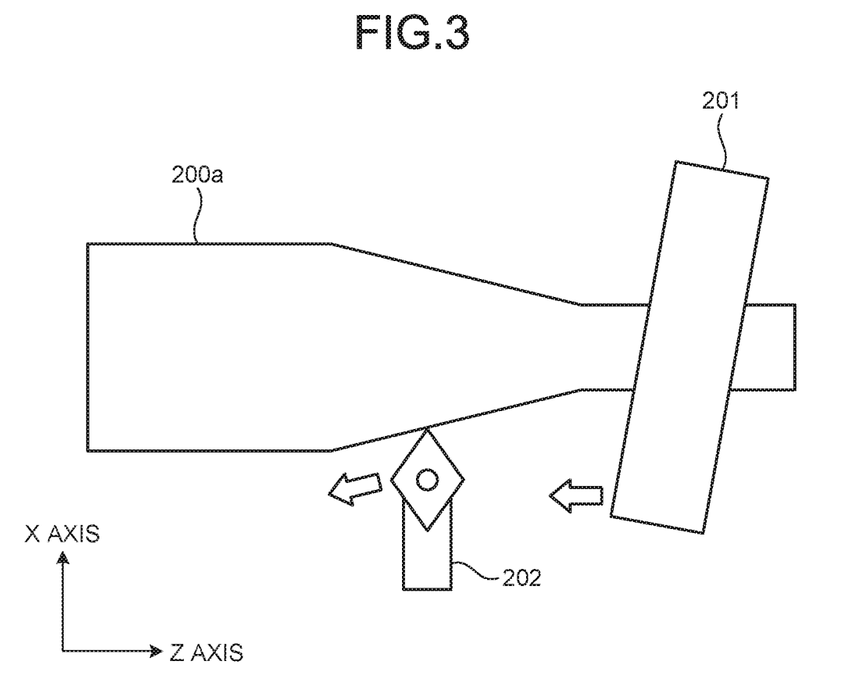
FIG. 3 is a schematic diagram illustrating a machining method performed by a numerical control apparatus according to the present embodiment.

FIG. 3 is a schematic diagram illustrating a machining method performed by a numerical control apparatus according to the present embodiment. As illustrated in FIG. 3, the numerical control apparatus according to the present embodiment performs thread whirling on a workpiece 200a using the thread whirling tool 201 and also performs turning on the workpiece 200a using a turning tool 202 simultaneously with thread whirling. Note that the range in which the thread whirling tool 201 performs machining does not interfere with the range in which the turning tool 202 performs machining. The rotation axis of the workpiece 200a is parallel to the illustrated Z axis. The rotation axis of the thread whirling tool 201 has an inclination with respect to the Z axis. The thread whirling tool 201 moves on the Z axis in the direction of the illustrated arrow while rotating, thereby machining the rotating workpiece. The turning tool 202 moves on the plane defined by the Z axis and the X axis orthogonal to the Z axis in the direction of the illustrated arrow, thereby machining the rotating workpiece.

The numerical control apparatus according to the present embodiment is described below. As described above, the numerical control apparatus according to the present embodiment controls the thread whirling tool 201 and the turning tool 202 illustrated in FIG. 3 to perform thread cutting on the workpiece 200a.

Figure 4:
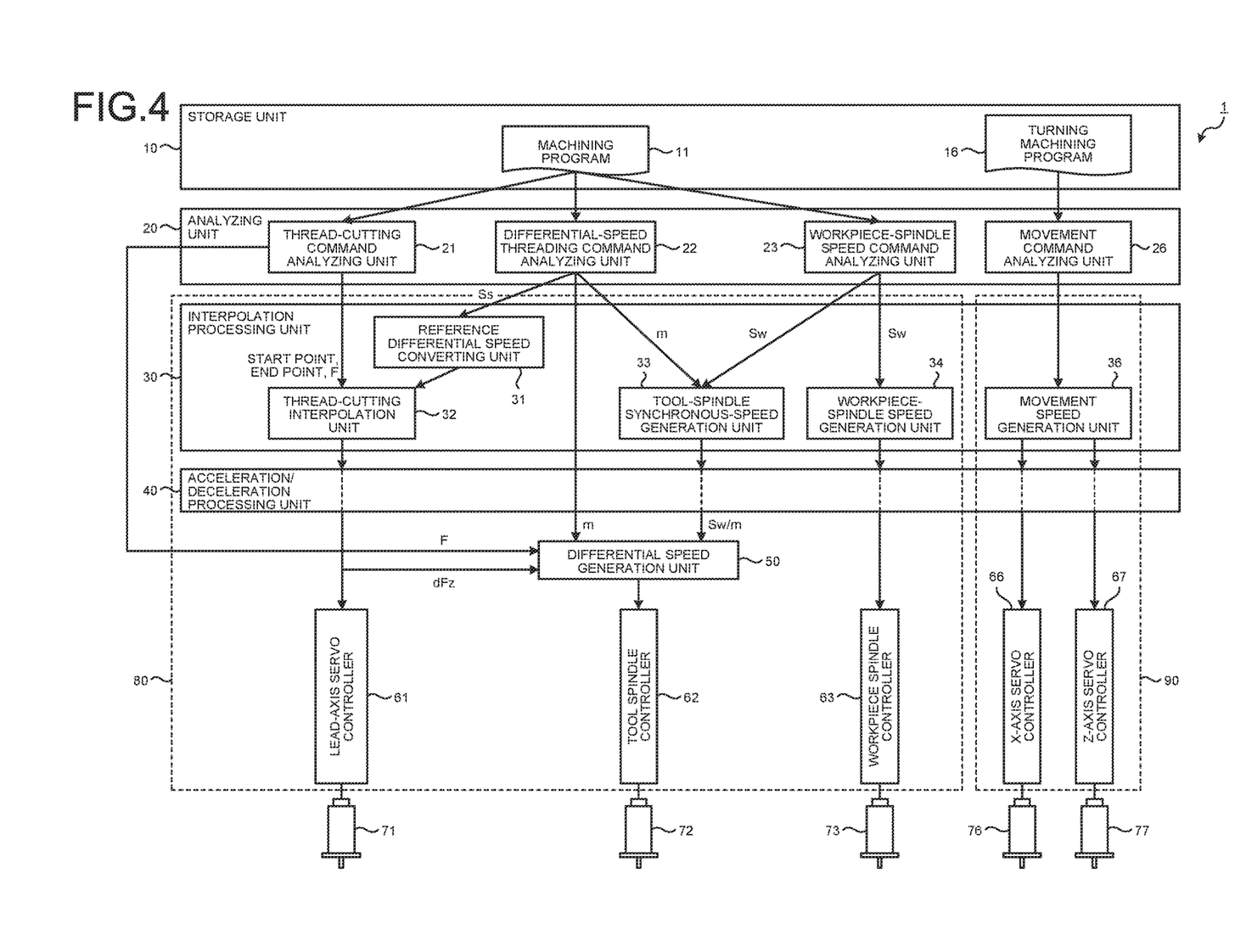
FIG. 4 is a diagram illustrating an example configuration of the numerical control apparatus according to the present embodiment.

FIG. 4 is a diagram illustrating an example configuration of the numerical control apparatus according to the present embodiment. As illustrated in FIG. 4, a numerical control apparatus 1 according to the present embodiment includes a storage unit 10; an analyzing unit 20; an interpolation processing unit 30; an acceleration/deceleration processing unit 40; a differential speed generation unit 50; a lead-axis servo controller 61; a tool spindle controller 62; a workpiece spindle controller 63; an X-axis servo controller 66; and a Z-axis servo controller 67. Motors 71 to 73, 76, and 77 are included in a machining apparatus to be controlled by the numerical control apparatus 1. In addition to the motors 71 to 73, 76 and 77, the machining apparatus to be controlled by the numerical control apparatus 1 includes a thread whirling tool and a turning tool similar to the thread whirling tool 201 and the turning tool 202 illustrated in FIG. 3.

The analyzing unit 20 of the numerical control apparatus 1 includes a thread-cutting command analyzing unit 21; a differential-speed threading command analyzing unit 22; a workpiece-spindle speed command analyzing unit 23; and a movement command analyzing unit 26. The interpolation processing unit 30 includes a reference differential speed converting unit 31; a thread-cutting interpolation unit 32; a tool-spindle synchronous-speed generation unit 33; a workpiece-spindle speed generation unit 34; and a movement speed generation unit 36. The storage unit 10 stores a machining program 11 and a turning machining program 16. The machining program 11 and the turning machining program 16 are numerical control (NC) programs for operating the numerical control apparatus 1. The machining program 11 causes the numerical control apparatus 1 to perform thread whirling, and the turning machining program 16 causes the numerical control apparatus 1 to perform turning. In the present embodiment, the numerical control program for operating the numerical control apparatus 1 is divided into the machining program 11 and the turning machining program 16. However, the blocks described in these two machining programs may be combined into one machining program so that the numerical control apparatus 1 is operated by one machining program.

Among the constituent elements of the numerical control apparatus 1, the thread-cutting command analyzing unit 21, the differential-speed threading command analyzing unit 22, the workpiece-spindle speed command analyzing unit 23, the reference differential speed converting unit 31, the thread-cutting interpolation unit 32, the tool-spindle synchronous-speed generation unit 33, the workpiece-spindle speed generation unit 34, the differential speed generation unit 50, the lead-axis servo controller 61, the tool spindle controller 62, and the workpiece spindle controller 63 are the constituent elements for causing the machining apparatus (not illustrated) to perform thread whirling. The reference differential speed converting unit 31, the thread-cutting interpolation unit 32, the tool-spindle synchronous-speed generation unit 33, the workpiece-spindle speed generation unit 34, the differential speed generation unit 50, the lead-axis servo controller 61, the tool spindle controller 62, and the workpiece spindle controller 63 constitute a thread-whirling motor controller 80. The movement command analyzing unit 26, the movement speed generation unit 36, the X-axis servo controller 66, and the Z-axis servo controller 67 are the constituent elements for causing the machining apparatus (not illustrated) to perform turning. The movement speed generation unit 36, the X-axis servo controller 66, and the Z-axis servo controller 67 constitute a turning motor controller 90.

The machining program 11 for causing the numerical control apparatus 1 to perform thread whirling includes a plurality of blocks representing various commands, such as a thread cutting command, a differential-speed threading command, and a workpiece-spindle speed command.

The thread cutting command includes a start point, an end point, and a thread lead F. The "start point" is a command value representing the point for starting thread cutting, that is, the position at which cutting by a thread whirling tool is started. The "end point" is a command value representing the point for ending thread cutting, that is, the position at which cutting by the thread whirling tool is ended. The "thread lead F" is a command value representing the movement amount of the thread whirling tool per rotation of a workpiece, that is, a command value representing how far the thread whirling tool is to be moved within one rotation of the workpiece.

The differential-speed threading command includes a reference differential speed Ss and the number of tool blades m. The "reference differential speed Ss" is a command value representing the difference between the reference rotational speed predetermined by a user and the rotational speed of the workpiece. The reference rotational speed is the rotational speed of a thread whirling tool when thread cutting is performed using the thread whirling tool having one blade. The rotational speed of a thread whirling tool in thread cutting is determined by the number of blades of the thread whirling tool. Specifically, in the case where machining is performed using thread whirling tools with different number of blades, the rotational speed of each thread whirling tool is determined such that all the thread whirling tools have the same period in which the blades of each thread whirling tool come into contact with and cut a workpiece. The "number of tool blades m" is a parameter representing the number of blades of the thread whirling tool.

The workpiece-spindle speed command includes a workpiece spindle speed Sw. The "workpiece spindle speed Sw" is a command value representing the rotational speed of the workpiece spindle, that is, the rotational speed of the workpiece.

The turning machining program 16 for causing the numerical control apparatus 1 to perform turning includes a plurality of blocks representing various commands, such as a movement command. The movement command designates the position of the turning tool and includes a position command value that is coordinates representing a position on the Z axis and the X axis at which a predetermined point of the turning tool or a predetermined point of a movable part that moves the turning tool is to be positioned.

The thread-cutting command analyzing unit 21 analyzes the thread cutting command included in the machining program 11, reads the start point, the end point, and the thread lead F, and outputs them to the thread-cutting interpolation unit 32. The thread-cutting command analyzing unit 21 further outputs the thread lead F to the differential speed generation unit 50.

The differential-speed threading command analyzing unit 22 analyzes the differential-speed threading command included in the machining program 11, reads and outputs the reference differential speed Ss to the reference differential speed converting unit 31, and reads and outputs the number of tool blades m to the tool-spindle synchronous-speed generation unit 33 and the differential speed generation unit 50.

The workpiece-spindle speed command analyzing unit 23 analyzes the workpiece-spindle speed command included in the machining program 11, reads the workpiece spindle speed Sw, and outputs it to the tool-spindle synchronous-speed generation unit 33 and the workpiece-spindle speed generation unit 34.

The movement command analyzing unit 26 analyzes the turning machining program 16, reads the position command value, and outputs it to the movement speed generation unit 36.

The reference differential speed converting unit 31 calculates a rotation pulse on the basis of the reference differential speed Ss input from the differential-speed threading command analyzing unit 22. The rotation pulse is the number of rotations per unit time. Thus, the reference differential speed converting unit 31 converts the reference differential speed Ss, which is the rotational speed, into the number of rotations per unit time. For example, when the unit time is 10 ms, the reference differential speed Ss is 3000 r/min, and the number of rotation pulses per rotation is 2000 pulses, the rotation pulses per unit time are 3000×2000/60/100=1000.

On the basis of the thread lead F input from the thread-cutting command analyzing unit 21 and the rotation pulses corresponding to the reference differential speed Ss calculated by the reference differential speed converting unit 31, the thread-cutting interpolation unit 32 calculates the lead-direction movement amount dFz of the thread whirling tool per unit time. The lead-direction movement amount dFz is obtained by multiplying the thread lead F by the rotation pulses. In a numerical control apparatus that performs conventional thread whirling, the movement amount of a thread whirling tool per unit time is obtained using the rotation rate of a spindle motor detected by an encoder attached to the spindle motor that rotates a workpiece. Thus, if the movement speed of the thread whirling tool is reduced to such an extent that thread cutting can be performed, the rotational speed of the workpiece is also reduced, and the rotational speed at which turning can be performed may not be maintained. In contrast, in the numerical control apparatus 1 according to the present embodiment, the movement speed of the thread whirling tool is determined by the reference differential speed Ss given by the differential-speed threading command. Thus, it is possible for the numerical control apparatus 1 to reduce the movement speed of a thread whirling tool while preventing the rotational speed of a workpiece from decreasing. The thread-cutting interpolation unit 32 calculates the rotational speed of the motor 71 that moves the thread whirling tool on the basis of the calculated movement amount dFz and outputs a control signal indicating the calculated rotational speed to the lead-axis servo controller 61. At this time, the thread-cutting interpolation unit 32 outputs the control signal indicating the calculated rotational speed over a time period determined on the basis of the start point and the end point input from the thread-cutting command analyzing unit 21. That is, the thread-cutting interpolation unit 32 outputs the control signal indicating the calculated rotational speed such that the thread whirling tool moves from the start point to the end point, where the start point and the end point are input from the thread-cutting command analyzing unit 21.

On the basis of the number of tool blades m input from the differential-speed threading command analyzing unit 22 and the workpiece spindle speed Sw input from the workpiece-spindle speed command analyzing unit 23, the tool-spindle synchronous-speed generation unit 33 calculates the basic rotational speed of the thread whirling tool and outputs the basic rotation amount dSt of the thread whirling tool per unit time. Specifically, the tool-spindle synchronous-speed generation unit 33 obtains the basic rotational speed by dividing the workpiece spindle speed Sw by the number of tool blades m. That is, $dSt=dSw/m$.

On the basis of the workpiece spindle speed Sw input from the workpiece-spindle speed command analyzing unit 23, the workpiece-spindle speed generation unit 34 calculates the rotational amount dSw of the workpiece spindle per unit time, which is the rotational speed of the motor 73 that rotates the workpiece.

On the basis of the position command value input from the movement command analyzing unit 26, the movement speed generation unit 36 calculates the movement amount of the turning tool per unit time in each of the X axis direction and the Z axis direction.

The acceleration/deceleration processing unit 40 adjusts and outputs the rotational speed of each corresponding motor or the movement speed of each corresponding tool input from the thread-cutting interpolation unit 32, the tool-spindle synchronous-speed generation unit 33, the workpiece-spindle speed generation unit 34, and the movement speed generation unit 36 so that each motor accelerates and decelerates with a predetermined operation pattern.

On the basis of the thread lead F input from the thread-cutting command analyzing unit 21, the lead-direction movement amount dFz of the thread whirling tool per unit time that has been adjusted by the acceleration/deceleration processing unit 40, the number of tool blades m input from the differential-speed threading command analyzing unit 22, and the basic rotational speed Sw/m that has been adjusted by the acceleration/deceleration processing unit 40, the differential speed generation unit 50 generates a rotational speed command value of the thread whirling tool.

The lead-axis servo controller 61 controls the motor 71 that moves the thread whirling tool such that the thread whirling tool moves by the lead-direction movement amount dFz per unit time that has been adjusted by the acceleration/deceleration processing unit 40.

The tool spindle controller 62 controls the motor 72 that rotates the thread whirling tool such that the thread whirling tool rotates at the rotational speed according to the rotational speed command value of the thread whirling tool input from the differential speed generation unit 50.

The workpiece spindle controller 63 controls the motor 73 that rotates the workpiece such that the workpiece rotates at the workpiece spindle speed that has been adjusted by the acceleration/deceleration processing unit 40.

The X-axis servo controller 66 controls the motor 76 that moves the turning tool in the X-axis direction such that the turning tool moves by the movement amount per unit time in the X-axis direction that has been adjusted by the acceleration/deceleration processing unit 40.

The Z-axis servo controller 67 controls the motor 77 that moves the turning tool in the Z-axis direction such that the turning tool moves by the movement amount per unit time in the Z-axis direction that has been adjusted by the acceleration/deceleration processing unit 40.

Next, operation of machining a workpiece by the numerical control apparatus 1 is described. The operation of turning by the numerical control apparatus 1 is similar to the turning operation by a conventional general numerical control apparatus, and the detailed description thereof is omitted. The numerical control apparatus 1 may perform turning by any known method. In the present embodiment, operation of thread whirling by the numerical control apparatus 1 is described.

Figure 5:
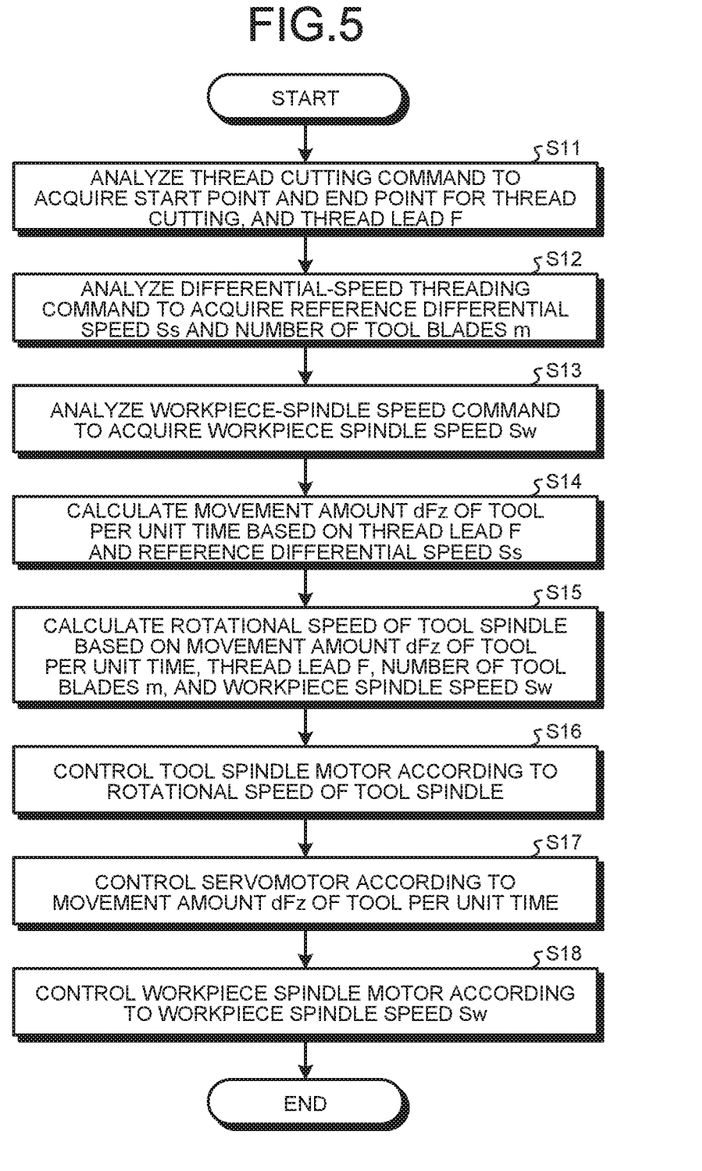
FIG. 5 is a flowchart illustrating an example operation of the numerical control apparatus according to the present embodiment.

FIG. 5 is a flowchart illustrating an example operation of the numerical control apparatus according to the present embodiment. FIG. 5 illustrates an operation procedure of thread whirling by the numerical control apparatus 1. The operation illustrated in FIG. 5 starts, for example, when an instruction operation for the start of machining is performed by a user.

When the operation starts, the numerical control apparatus 1 first analyzes a thread cutting command with the thread-cutting command analyzing unit 21 to acquire the start point and the end point for thread cutting and the thread lead F (step S11). The numerical control apparatus 1 analyzes a differential-speed threading command with the differential-speed threading command analyzing unit 22 to acquire the reference differential speed Ss and the number of tool blades m (step S12). The numerical control apparatus 1 analyzes a workpiece-spindle speed command with the workpiece-spindle speed command analyzing unit 23 to acquire the workpiece spindle speed Sw (step S13). Note that, the order of steps S11 to S13 may be interchanged.

Next, the numerical control apparatus 1 calculates, on the basis of the thread lead F and the reference differential speed Ss, a lead-direction speed Fz of the thread whirling tool to calculate the lead-direction movement amount dFz of the thread whirling tool per unit time (step S14). Note that Fz=F×Ss. As described above, the lead-direction movement amount dFz of the thread whirling tool per unit time is calculated by the thread-cutting interpolation unit 32.

Next, the numerical control apparatus 1 calculates the rotational speed of the tool spindle on the basis of the lead-direction movement amount dFz of the thread whirling tool per unit time, the thread lead F, the number of tool blades m, and the workpiece spindle speed Sw (step S15). In step S15, first, the tool-spindle synchronous-speed generation unit 33 calculates the basic rotational speed of the thread whirling tool. Next, the differential speed generation unit 50 calculates, on the basis of the lead-direction movement amount dFz of the thread whirling tool per unit time, the thread lead F, and the number of tool blades m, the rotation amount dSs' per unit time synchronized with the lead-direction movement amount dFz per unit time that has been adjusted by the acceleration/deceleration processing unit 40. Then, the differential speed generation unit 50 superposes the calculated rotation amount dSs' per unit time on the basic rotation amount dSt of the thread whirling tool per unit time generated by the tool-spindle synchronous-speed generation unit 33 and adjusted by the acceleration/deceleration processing unit 40. The rotation amount dSs' per unit time calculated by the differential speed generation unit 50 is expressed by dSs'=dFz'/(F×m). The calculation formula of the rotational speed Ss' calculated by the differential speed generation unit 50 after the acceleration is completed and the speed becomes constant is expressed by following Formula (1).

$$Ss'=Fz/(F \times m)=(Ss \times F)/(F \times m)=Ss/m \qquad (1)$$

The differential speed generation unit 50 outputs, to the tool spindle controller 62, a command value representing the rotational speed obtained by superposing the rotational speed Ss' on the basic rotational speed (Sw/m). The differential speed generation unit 50 superposes the rotation amount dSs' per unit time on the basic rotation amount dSt of the thread whirling tool per unit time generated by the tool-spindle synchronous-speed generation unit 33 and adjusted by the acceleration/deceleration processing unit 40 to generate a command value. The rotational speed of the tool spindle, which is the command value output to the tool spindle controller 62 by the differential speed generation unit 50 after the acceleration is completed and the speed becomes constant, is expressed by following Formula (2).

$$(\text{Rotational speed of tool spindle})=Sw/m+Ss/m \qquad (2)$$

Next, the numerical control apparatus 1 controls the motor 72, which is a tool spindle motor, according to the rotational speed of the tool spindle (step S16). The numerical control apparatus 1 controls the motor 71, which is a servomotor, according to the lead-direction movement amount dFz of the tool per unit time (step S17). The numerical control apparatus 1 controls the motor 73, which is a workpiece spindle motor, according to the workpiece spindle speed Sw (step S18).

Figure 6:
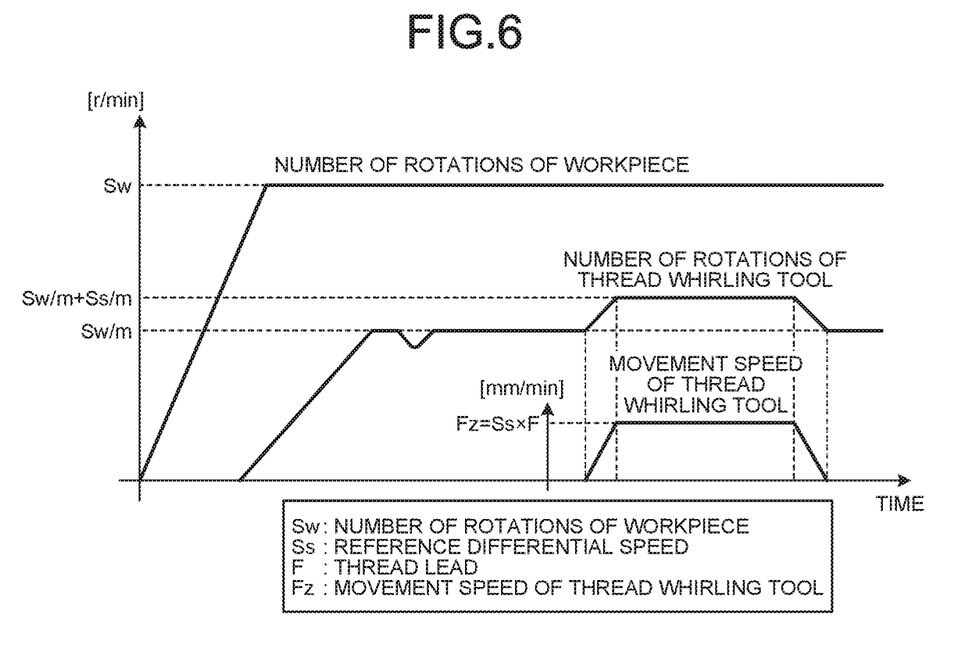
FIG. 6 is a diagram illustrating an example of the relation between the number of rotations of a workpiece and the number of rotations and movement speed of a thread whirling tool in thread whirling performed by the numerical control apparatus according to the present embodiment.

As described above, in the thread whirling by the numerical control apparatus 1, the movement amount of the thread whirling tool per unit time, that is, the movement speed is determined by the reference differential speed Ss given by the differential-speed threading command. The rotational speed of the thread whirling tool is determined by the movement amount of the thread whirling tool per unit time, the number of tool blades, and the rotational speed of the workpiece. Thus, the relation between the rotational speed of the workpiece, the rotational speed of the thread whirling tool, and the movement speed of the thread whirling tool is as illustrated in FIG. 6. FIG. 6 is a diagram illustrating an example of the relation between the number of rotations of the workpiece and the number of rotations and the movement speed of the thread whirling tool in thread whirling performed by the numerical control apparatus according to the present embodiment. Since the number of rotations of the thread whirling tool is increased by Ss/m while the thread whirling tool is moving, the reference differential speed Ss included in the differential-speed threading command is set to a value such that the number of rotations in the thread cutting (while the thread whirling tool is moving at a constant speed) (Sw/m+Ss/m) becomes an appropriate number of rotations. Note that, the reason that the number of rotations of the thread whirling tool temporarily decreases after it reaches Sw/m is to make an adjustment for matching the reference rotation position of the workpiece with the reference rotation position of the thread whirling tool.

As described above, the numerical control apparatus 1 according to the present embodiment includes the thread-cutting command analyzing unit 21 that analyzes a thread cutting command to acquire a start point and an end point for thread cutting and a thread lead F representing the lead-direction movement amount of a thread whirling tool per rotation of a workpiece; the differential-speed threading command analyzing unit 22 that analyzes a differential-speed threading command to acquire the reference differential speed Ss representing the difference between the rotational speed of the thread whirling tool when the thread cutting is performed using a thread whirling tool having one blade and the rotational speed of the workpiece, and the number of tool blades m of the thread whirling tool; and the workpiece-spindle speed command analyzing unit 23 that analyzes a workpiece-spindle speed command to acquire the workpiece spindle speed Sw representing the rotational speed of the workpiece when the thread cutting is performed. The numerical control apparatus 1 calculates, on the basis of the thread lead F and the reference differential speed Ss, the lead-direction movement amount dFz of the thread whirling tool per unit time, that is, the movement speed Fz and controls the motor 71 that moves the thread whirling tool such that the thread whirling tool moves at the calculated movement speed Fz. The numerical control apparatus 1 calculates, on the basis of the thread lead F, the reference differential speed Ss, the number of tool blades m, and the workpiece spindle speed Sw, the rotational speed of the tool spindle and controls the motor 72 that rotates the thread whirling tool such that the thread whirling tool rotates at the calculated rotational speed.

In the numerical control apparatus 1 according to the present embodiment, the movement speed of the thread whirling tool is determined by the thread lead F and the reference differential speed Ss, and the movement speed of the thread whirling tool does not change even when the rotational speed of the workpiece changes. Thus, it is possible for the numerical control apparatus 1 to increase the rotational speed of the workpiece while preventing the movement speed of the thread whirling tool from increasing. For this reason, by applying the numerical control apparatus 1, it is possible to perform turning while a thread groove is accurately machined and to thus efficiently perform machining for forming a screw.

In the present embodiment, it has been described that a differential-speed threading command includes the number of tool blades m and the reference differential speed Ss. However, the reference differential speed Ss can also be obtained by calculation. In this case, the differential-speed threading command includes only the number of tool blades m. The reference differential speed Ss can be calculated according to following Formula (3).

$$Ss = m \times St - Sw \qquad (3)$$

In Formula (3), St is the basic rotational speed of the thread whirling tool and can be obtained from the basic rotation amount dSt of the thread whirling tool per unit time described above. The reference differential speed Ss is calculated by, for example, the reference differential speed converting unit 31. In this case, the number of tool blades m is input from the differential-speed threading command analyzing unit 22 to the reference differential speed converting unit 31, and the workpiece spindle speed Sw is input from the workpiece-spindle speed command analyzing unit 23 to the reference differential speed converting unit 31. The basic rotational speed St of the thread whirling tool may be given by a differential-speed threading command. In this case, the differential-speed threading command has a configuration including the basic rotational speed St of the thread whirling tool instead of the reference differential speed Ss, that is, a configuration including the number of tool blades m and the basic rotational speed St of the thread whirling tool.

The numerical control apparatus 1 according to the present embodiment can simultaneously perform thread whirling and turning, but thread whirling and turning do not necessarily need to be performed simultaneously to machine a workpiece. The user can change the configuration of the program to be input to the numerical control apparatus 1 such that only thread whirling is performed or only turning is performed.

Figure 7:
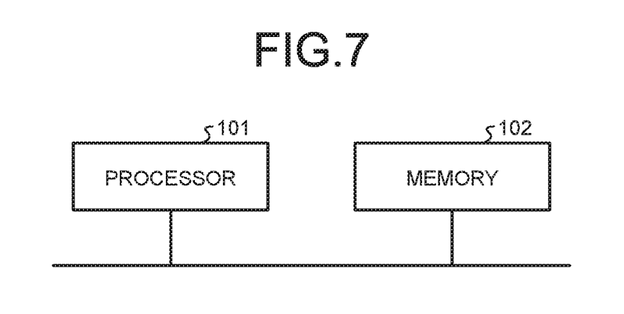
FIG. 7 is a diagram illustrating an example configuration of hardware that implements the numerical control apparatus according to the present embodiment.

Next, a configuration of hardware implementing the numerical control apparatus 1 is described. FIG. 7 is a diagram illustrating an example configuration of hardware that implements the numerical control apparatus according to the present embodiment.

The numerical control apparatus 1 can be implemented by hardware including a processor 101 and a memory 102 illustrated in FIG. 7. The processor 101 is, for example, a Central Processing Unit (also referred to as a CPU, a processing unit, an arithmetic unit, a microprocessor, a microcomputer, a processor, a Digital Signal Processor (DSP)) or a system Large Scale Integration (LSI), or the like. The memory 102 is, for example, a Random Access Memory (RAM), a Read Only Memory (ROM), a flash memory, an Erasable Programmable ROM (EPROM), or an Electrically Erasable Programmable ROM (EEPROM) (registered trademark). The hardware that implements the numerical control apparatus 1 may further include a display device, an input device, a communication device, and the like.

The analyzing unit 20, the interpolation processing unit 30, the acceleration/deceleration processing unit 40, the differential speed generation unit 50, the lead-axis servo controller 61, the tool spindle controller 62, the workpiece spindle controller 63, the X-axis servo controller 66, and the Z-axis servo controller 67 of the numerical control apparatus 1 can each be implemented by the processor 101 loading and executing a corresponding program from the memory 102. The storage unit 10 of the numerical control apparatus 1 can be implemented by the memory 102.

The configurations described in the above embodiment are merely examples of an aspect of the present invention and can be combined with other known techniques, and part of the configurations can be omitted or changed without departing from the gist of the present invention.

REFERENCE SIGNS LIST

1 numerical control apparatus; 10 storage unit; 11 machining program; 16 turning machining program; 20 analyzing unit; 21 thread-cutting command analyzing unit; 22 differential-speed threading command analyzing unit; 23 workpiece-spindle speed command analyzing unit; 26 movement command analyzing unit; 30 interpolation processing unit; 31 reference differential speed converting unit; 32 thread-cutting interpolation unit; 33 tool-spindle synchronous-speed generation unit; 34 workpiece-spindle speed generation unit; 36 movement speed generation unit; 40 acceleration/deceleration processing unit; 50 differential speed generation unit; 61 lead-axis servo controller; 62 tool spindle controller; 63 workpiece spindle controller; 66 X-axis servo controller; 67 Z-axis servo controller; 71 to 73, 76, 77 motor; 80 thread-whirling motor controller; 90 turning motor controller.

The invention claimed is:

1. A numerical control apparatus comprising:
thread-whirling motor control circuitry configured to control, on a basis of a thread lead representing a movement amount of a thread whirling tool per rotation of a workpiece, a reference differential speed representing a difference between a predetermined reference rotational speed of the thread whirling tool and a rotational speed of the workpiece, a number of tool blades representing a number of blades of the thread whirling tool, and a workpiece spindle speed representing the rotational speed of the workpiece, a motor that moves the thread whirling tool, a motor that rotates the thread whirling tool, and a motor that rotates the workpiece,
wherein the thread-whirling motor control circuitry:
calculates movement speed of the thread whirling tool on a basis of the thread lead and the reference differential speed and controls the motor that moves the thread whirling tool such that the thread whirling tool moves at the calculated movement speed;
calculates rotational speed of a spindle of the thread whirling tool on a basis of the thread lead, the reference differential speed, the number of tool blades, and the workpiece spindle speed and controls the motor that rotates the thread whirling tool such that the thread whirling tool rotates at the calculated rotational speed; and
controls the motor that rotates the workpiece on a basis of the workpiece spindle speed.

2. The numerical control apparatus according to claim 1, further comprising:
thread-cutting command analyzing circuitry configured to analyze a thread cutting command to acquire the thread lead;
differential-speed threading command analyzing circuitry configured to analyze a differential-speed threading command to acquire the reference differential speed and the number of tool blades; and
workpiece-spindle speed command analyzing circuitry configured to analyze a workpiece-spindle speed command to acquire the workpiece spindle speed.

3. The numerical control apparatus according to claim 2, further comprising:
movement command analyzing circuitry configured to analyze a movement command including a position command value representing a position of a turning tool; and
turning motor control circuitry to control a motor that moves the turning tool on a basis of the position command value.

4. The numerical control apparatus according to claim 3, wherein:
the thread-whirling motor control circuitry calculates a movement amount of the thread whirling tool per unit time on a basis of the thread lead and the reference differential speed, controls the motor that moves the thread whirling tool on a basis of the calculated movement amount, calculates a rotational speed of the thread whirling tool on a basis of the calculated movement amount, the thread lead, the number of tool blades, and the workpiece spindle speed, controls the motor that rotates the thread whirling tool on a basis of the calculated rotational speed, and controls the motor that rotates the workpiece on a basis of the workpiece spindle speed.

5. The numerical control apparatus according to claim 2, wherein:
the thread-whirling motor control circuitry calculates a movement amount of the thread whirling tool per unit time on a basis of the thread lead and the reference differential speed, controls the motor that moves the thread whirling tool on a basis of the calculated movement amount, calculates a rotational speed of the thread whirling tool on a basis of the calculated movement amount, the thread lead, the number of tool blades, and the workpiece spindle speed, controls the motor that rotates the thread whirling tool on a basis of the calculated rotational speed, and controls the motor that rotates the workpiece on a basis of the workpiece spindle speed.

6. The numerical control apparatus according to claim 1, further comprising:
thread-cutting command analyzing circuitry configured to analyze a thread cutting command to acquire the thread lead;
differential-speed threading command analyzing circuitry configured to analyze a differential-speed threading command to acquire the number of tool blades and the reference rotational speed of the thread whirling tool; and
workpiece-spindle speed command analyzing circuitry to analyze a workpiece-spindle speed command to acquire the workpiece spindle speed,
wherein the thread-whirling motor control circuitry calculates the reference differential speed on a basis of the number of tool blades, the reference rotational speed of the thread whirling tool, and the workpiece spindle speed.

7. The numerical control apparatus according to claim 6, further comprising:
movement command analyzing circuitry to analyze a movement command including a position command value representing a position of a turning tool; and
turning motor control circuitry to control a motor that moves the turning tool on a basis of the position command value.

8. The numerical control apparatus according to claim 7, wherein:
the thread-whirling motor control circuitry calculates a movement amount of the thread whirling tool per unit time on a basis of the thread lead and the reference differential speed, controls the motor that moves the thread whirling tool on a basis of the calculated movement amount, calculates a rotational speed of the thread whirling tool on a basis of the calculated movement amount, the thread lead, the number of tool blades, and the workpiece spindle speed, controls the motor that rotates the thread whirling tool on a basis of the calculated rotational speed, and controls the motor that rotates the workpiece on a basis of the workpiece spindle speed.

9. The numerical control apparatus according to claim 6, wherein:
the thread-whirling motor control circuitry calculates a movement amount of the thread whirling tool per unit time on a basis of the thread lead and the reference differential speed, controls the motor that moves the thread whirling tool on a basis of the calculated movement amount, calculates a rotational speed of the thread whirling tool on a basis of the calculated movement amount, the thread lead, the number of tool blades, and the workpiece spindle speed, controls the motor that rotates the thread whirling tool on a basis of the calculated rotational speed, and controls the motor that rotates the workpiece on a basis of the workpiece spindle speed.

10. The numerical control apparatus according to claim 1, further comprising:
movement command analyzing circuitry to analyze a movement command including a position command value representing a position of a turning tool; and
turning motor control circuitry to control a motor that moves the turning tool on a basis of the position command value.

11. The numerical control apparatus according to claim 10, wherein:
the thread-whirling motor control circuitry calculates a movement amount of the thread whirling tool per unit time on a basis of the thread lead and the reference differential speed, controls the motor that moves the thread whirling tool on a basis of the calculated movement amount, calculates a rotational speed of the thread whirling tool on a basis of the calculated movement amount, the thread lead, the number of tool blades, and the workpiece spindle speed, controls the motor that rotates the thread whirling tool on a basis of the calculated rotational speed, and controls the motor that rotates the workpiece on a basis of the workpiece spindle speed.

12. The numerical control apparatus according to claim 1, wherein:
the thread-whirling motor control circuitry calculates a movement amount of the thread whirling tool per unit time on a basis of the thread lead and the reference differential speed, controls the motor that moves the thread whirling tool on a basis of the calculated movement amount, calculates a rotational speed of the thread whirling tool on a basis of the calculated movement amount, the thread lead, the number of tool blades, and the workpiece spindle speed, controls the motor that rotates the thread whirling tool on a basis of the calculated rotational speed, and controls the motor that rotates the workpiece on a basis of the workpiece spindle speed.

13. The numerical control apparatus according to claim 1, wherein:
the movement speed of the thread whirling tool is capable of being reduced without reducing the rotational speed of the workpiece.

14. The numerical control apparatus according to claim 1, wherein:
the movement speed of the thread whirling tool is obtained by multiplying the thread lead by the reference differential speed.

15. The numerical control apparatus according to claim 1, wherein:
the rotational speed of the spindle of the thread whirling tool is obtained by superposing a value, obtained by dividing the reference differential speed by the number of tool blades, on a value, obtained by dividing the workpiece spindle speed by the number of tool blades.

16. A machining method for performing thread cutting by a numerical control apparatus controlling a machining apparatus including a thread whirling tool, the machining method comprising:
analyzing a thread cutting command including a thread lead representing a movement amount of the thread whirling tool per rotation of a workpiece;
analyzing a differential-speed threading command including a reference differential speed representing a difference between a predetermined reference rotational speed of the thread whirling tool and a rotational speed of the workpiece, and a number of tool blades representing a number of blades of the thread whirling tool;
analyzing a workpiece-spindle speed command including a workpiece spindle speed representing the rotational speed of the workpiece;
calculating movement speed of the thread whirling tool on a basis of the thread lead and the reference differential speed and controlling the motor that moves the thread whirling tool such that the thread whirling tool moves at the calculated movement speed;
calculating rotational speed of a spindle of the thread whirling tool on a basis of the thread lead, the reference differential speed, the number of tool blades, and the workpiece spindle speed and controlling the motor that rotates the thread whirling tool such that the thread whirling tool rotates at the calculated rotational speed; and
controlling a motor that rotates the workpiece on a basis of the workpiece spindle speed.

* * * * *